US00PP36516P2

(12) United States Plant Patent
Thompson et al.

(10) Patent No.: US PP36,516 P2
(45) Date of Patent: Mar. 4, 2025

(54) BLACKBERRY PLANT NAMED 'HFG B1902T'

(50) Latin Name: ***Rubus* L. subgenus *Rubus***
Varietal Denomination: HFG B1902T

(71) Applicant: Hortifrut Genetics Limited, Dublin (IE)

(72) Inventors: Ellen Thompson, Watsonville, CA (US); Max Laddon, Santa Cruz, CA (US)

(73) Assignee: Hortifrut Genetics Limited, Dublin (IE)

( * ) Notice: Subject to any disclaimer, the term of this patent is extended or adjusted under 35 U.S.C. 154(b) by 0 days.

(21) Appl. No.: 18/638,490

(22) Filed: Apr. 17, 2024

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203, 204
See application file for complete search history.

*Primary Examiner* — Susan McCormick Ewoldt
(74) *Attorney, Agent, or Firm* — King IP Law; Joshua King

(57) ABSTRACT

A new and distinct cultivar of blackberry named 'HFG B1902T' is characterized by a concentrated early peak of production of consistently shaped, medium ovate fruit borne on spineless erect floricanes. This new cultivar is identified, among other things, by its long fruiting laterals, thick cane diameter, consistent high percentage of soluble solids (Brix), firmness, and low color reversion during postharvest evaluations.

4 Drawing Sheets

Latin name of the genus and species of the plant claimed: *Rubus* L. subgenus *Rubus*.

Variety Denomination: 'HFG B1902T'.

BACKGROUND OF THE INVENTION

Blackberries are a commercially important member of the Rosaceae (rose) family, Rosoideae subfamily, known botanically as *Rubus* L. subgenus *Rubus* Watson. Rosaceae is considered the sixth most economically important crop family which includes apple, almond, cherry, peach, plum, raspberry and strawberry, among many others.

Plants in the *Rubus* genus are unique in that they have perennial root systems from which biennial canes are borne. Like raspberries (*Rubus idaeus*), blackberry fruits are formed by an aggregation of individual drupelets attached to a fleshy torus (receptacle). Unlike raspberries, the torus remains connected to the blackberry drupelets upon harvest, and is consumed. Each drupelet contains a seed (pyrene), that is surrounded by a fleshy mesocarp (pulp) and exocarp (fruit skin). Blackberries are well-documented for their health benefits and a known source for secondary plant metabolites including anthocyanins, phenolics, tannins and flavonoids. Worldwide blackberries are wild-collected, cultivated, and consumed as jams, jellies, juice, frozen and fresh products.

Production of fresh-market blackberries has expanded significantly over the past 25 years, and fruits are now in demand globally. Floricane-fruiting blackberries have shown broad adaptation to both temperate and tropical environments, allowing production to span across diverse growing zones. This adaptation, along with selection pressure for firmness and improved organoleptic characteristics has allowed for blackberries to be shipped internationally to the high-demand markets in North America and across Europe.

Seeds of the present cultivar, 'HFG B1902T', were created from a controlled cross using hand pollination. The female parent is the proprietary 'Ponca', marketed under the 'Sweet-Ark™ Ponca' tradename (U.S. Plant Pat. No. 33,330 P2) and released by the University of Arkansas. The male parent used in the controlled cross was selection 'A-2596T' (unpatented, this selection is also from the University of Arkansas). This cross was created in 2017 in Watsonville, Santa Cruz County, California, USA. Seeds from this controlled pollination were extracted, germinated, and sowed in spring 2018. In 2019, a plant within this seedling family with superior characteristics was identified and designated as selection 'HFG B1902T'. Test plots of 'HFG B1902T' were subsequently planted for evaluation and deemed to be unique, distinct, stable and desirable for fresh-market characteristics.

'HFG B1902T' differs from its female parent 'Ponca' in vigor. General indicators of vigor include number of canes per crown and cane height achieved during the first year of establishment. 'HFG B1902T' produces 8-10 canes per crown while 'Ponca' produces 4-6 canes. Cane height during the year of establishment commonly reaches approximately 2.4 m in the present cultivar, while 'Ponca' cane height reaches approximately 1.8 m.

'HFG B1902T' is similar to it's male parent 'A-2596T' in terms of vigor, yet differs greatly in fruit characteristics. Average berry weight for 'HFG B1902T' is 6.9 g, while 'A-2596T' is 9.7 g. Another marked difference is in soluble solids content (%), where 'HFG B1902T' averages 13.2% while 'A-2596T' averages 10.2%.

'HFG B1902T' offers significant advantages over the existing, patented floricane-fruiting blackberry variety 'Columbia Giant' (U.S. Plant Pat. No. 28,369 P3). Another example of an existing, patented floricane-fruiting blackberry variety is 'A-2454T' (U.S. Plant Pat. No. 32,965 P2). A further example of an existing floricane-fruiting blackberry variety is 'Caddo' (U.S. Plant Pat. No. 33,115 P2).

Compared to 'Columbia Giant', which has a trailing growth habit, the present cultivar has an erect growth habit, requiring less labor to train the canes in a typical blackberry trellis system.

Compared with 'A-2454T' (1.25 kg/plant), productivity of the present cultivar (2.49 kg/plant) is significantly higher when both were trialed in Watsonville, Santa Cruz County, California, USA.

Compared to 'Caddo' (9.8%), the present cultivar has a higher (13.2%) soluble solids (Brix) content when grown in Watsonville, Santa Cruz County, California, USA.

Thus, 'HFG B1902T' is a new and distinct floricane-fruiting blackberry cultivar that can be identified, among other things, by its erect growth habit, less intensive cane management needs, higher yields and increased soluble solids.

BRIEF DESCRIPTION OF THE PHOTOGRAPHS

DETAILED DESCRIPTION

Figure 1:
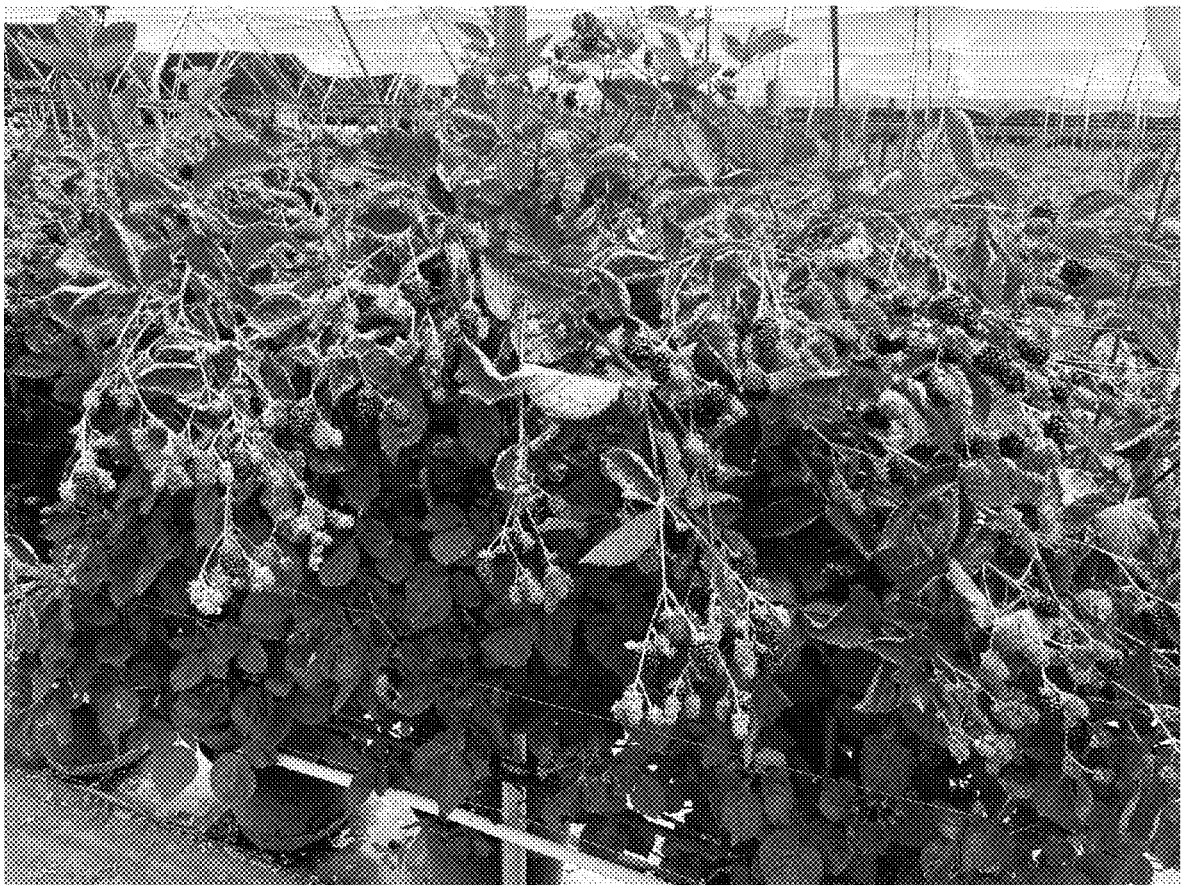
FIG. 1 is a photograph showing the typical cropload and distribution of berries on floricanes of 'HFG B1902T'.
Figure 2:
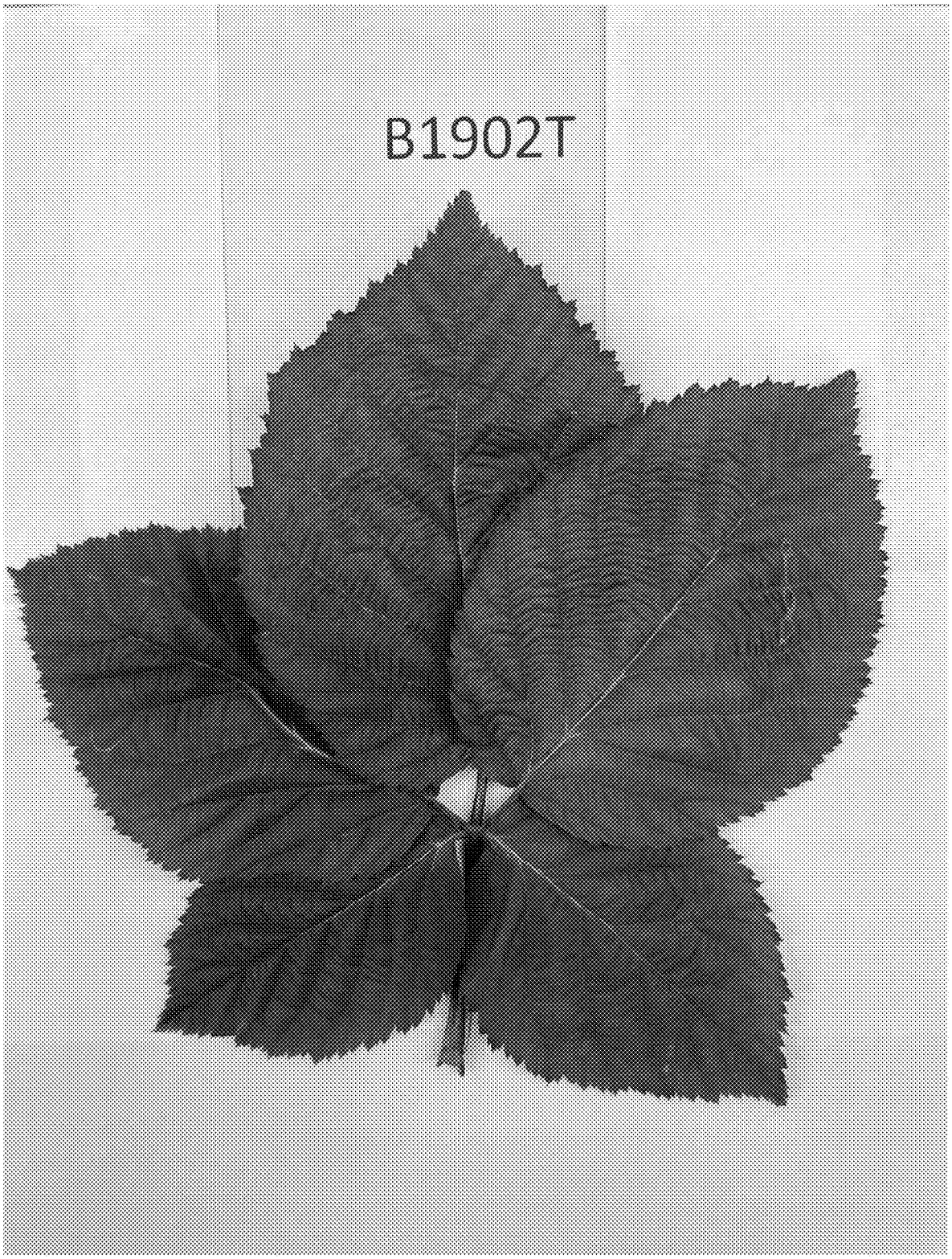
FIG. 2 is a photograph of a typical pentafoliate leaflet borne from vegetative buds found on 'HFG B1902T'.
Figure 3:
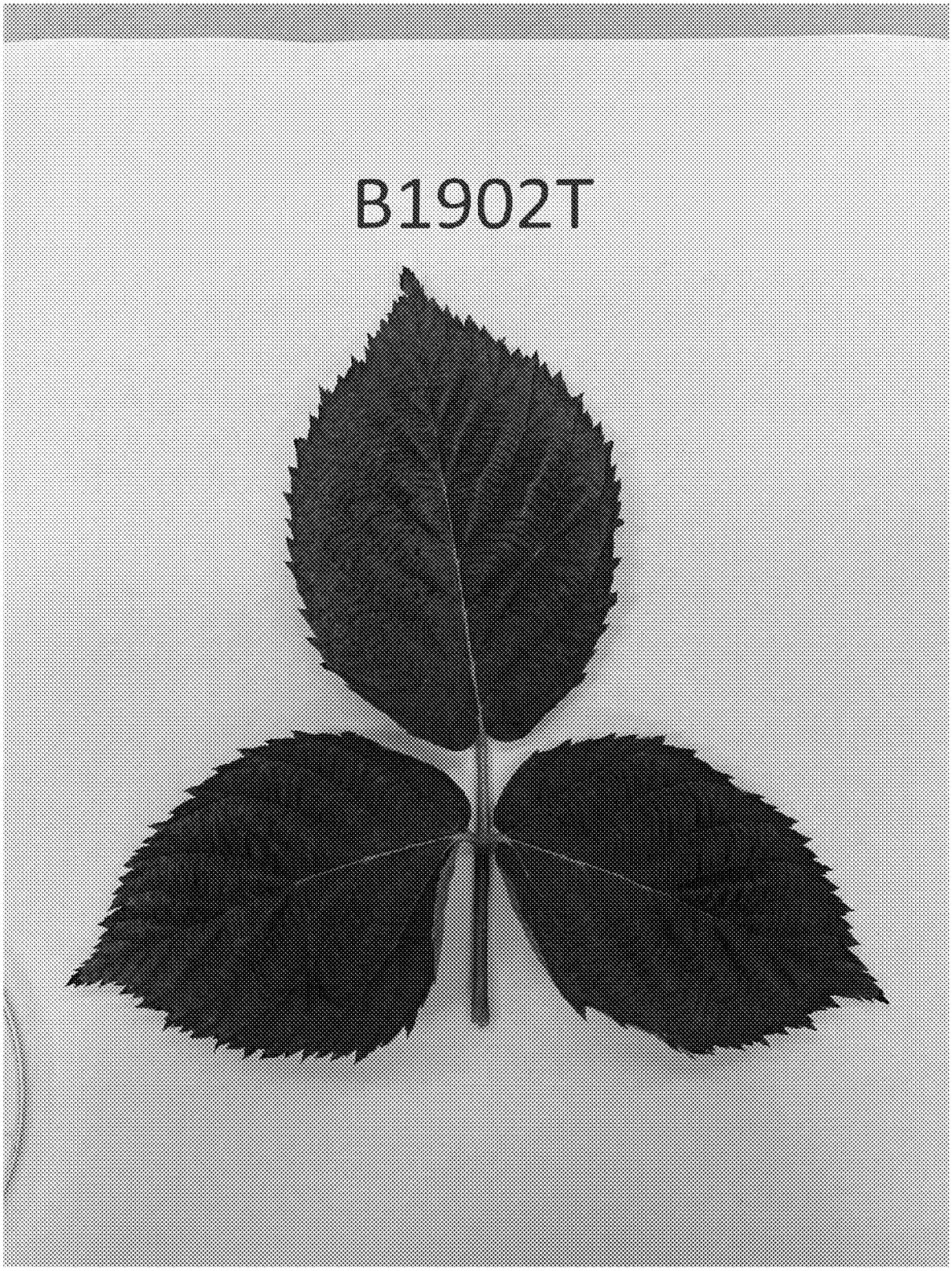
FIG. 3 is a photograph of a typical trifoliate leaflet borne from reproductive buds found on 'HFG B1902T'.
Figure 4:
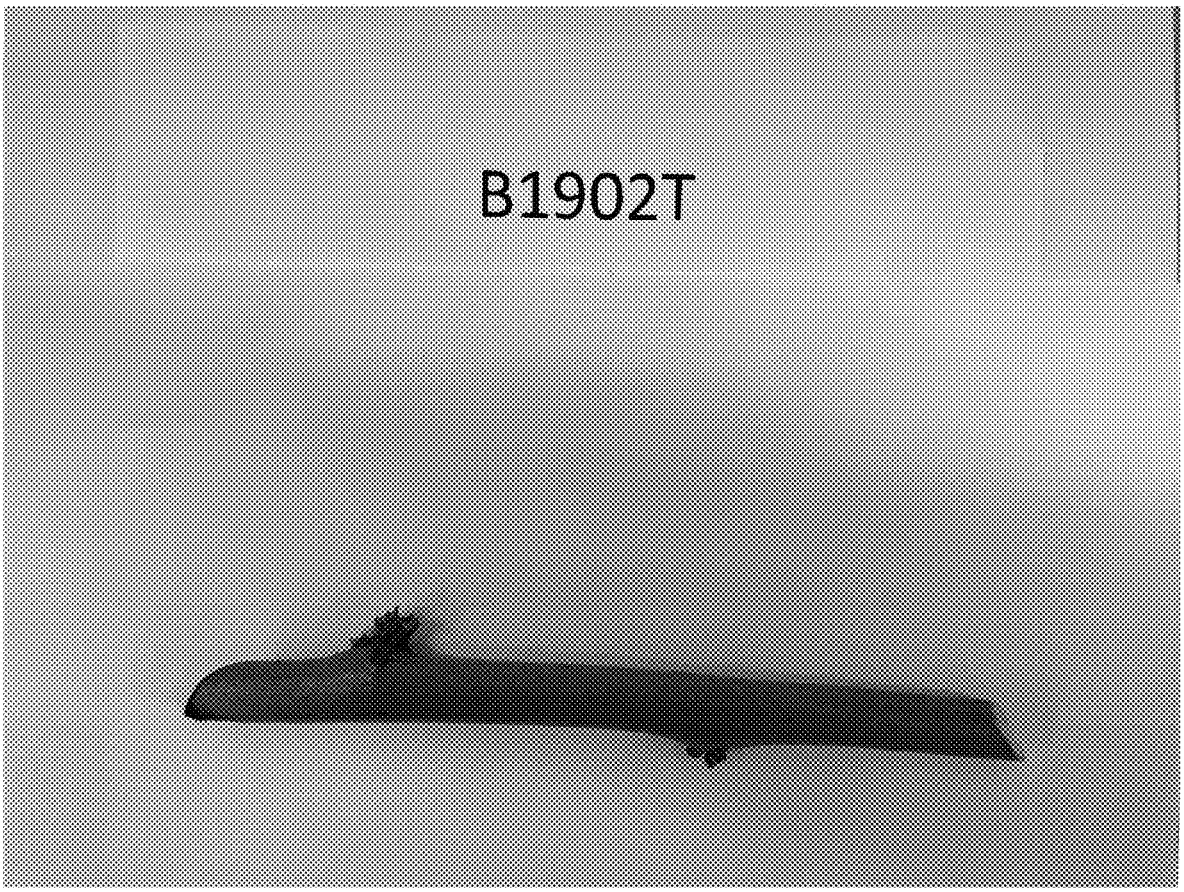
FIG. 4 is a photograph of a typical spineless cane of 'HFG B1902T'.

Note: statements of characteristics herein represent exemplary observations of the cultivar herein and will vary depending on time of year, location, annual weather, etc.

Cultivar name: 'HFG B1902T'.

Classification:

*Family*.—Rosaceae.

Botanical name: *Rubus* L. subgenus *Rubus*.

*Common name*.—Blackberry. Although blackberries (*Rubus* subgenus *Rubus* Watson) are highly heterogeneous and outcrossing and most clones contain genes from more than one species, the new cultivar and its progenitor lines phenotypically exhibit characters predominately of the erect eastern United States species, *Rubus allegheniensis* Porter (highbush blackberry).

Parentage:

*Female parent*.—'Ponca' (U.S. Plant Pat. No. 33,330 P2).

*Male parent*.—A-2596T (unpatented). 'HFG B1902T' was first identified in a substrate block with other seedlings in July 2019 at Watsonville, Santa Cruz County, California, USA. 'HFG B1902T' was first propagated asexually by crown division in November 2020 in Watsonville, CA USA. The crown on the original plant was separated into basal cane pieces (approximately 15 cm long) with root pieces attached and replanted into a single larger pot and placed inside a screenhouse on site. The remaining root pieces were chilled for 4 weeks, then planted inside a heated greenhouse to force adventitious shoots. Approximately 10 adventitious shoots were excised, rooted, and planted the following spring for further evaluation of the selection. In June 2022, five young actively growing primocanes were excised and shipped to McMinnville, Yamhill County, Oregon, USA, where vegetative material was explanted and established in vitro for micropropagation. This tissue culture propagation method has allowed for additional, more extensive testing of 'HFG B1902T' and aided in determining that this cultivar is genetically stable.

Growing location for the observations herein: Watsonville, California, Santa Cruz County, USA.

Time of year (season): Spring and Autumn 2023.

Age of plants used for this discussion: 6 months for primocanes, 14 months for floricanes.

Age of plants used for the photographs in the figures: 6 months for primocanes, 14 months for floricanes.

Type of greenhouse covering or growing structure, or field: Substrate block with high tunnel over plants.

Light: Natural.

Pinch dates (if required): Not required.

Color terminology where noted were followed using The R.H.S. Colour Chart, Royal Horticultural Society, Fifth Edition, London, United Kingdom (2007).

Observations for floricanes herein were made in May 2023. Observations for primocanes herein were made in November 2023.

Plant:

*Form/shape*.—Vase/Upright.

*Growth habit*.—Erect.

*Height*.—102.24 cm as measured from cane base to cane apex.

*Spread*.—68.58 cm as measured from lateral leaf tip to lateral leaf tip.

*Propagation method*.—Tissue culture (in vitro).

*Time to initiate and develop roots*.—30 days.

*Root description*.—Fibrous.

Primocanes:

*Cane shape in cross-section*.—Rounded to angular.

*Diameter*.—Base: 1.7 cm|Middle: 1.0 cm|Tip: 0.3 cm.

*Length*.—297.9 cm.

*Number of nodes*.—109.

*Internode length*.—Base: 4.8 cm|Middle: 8.8 cm|Tip: 3.9 cm.

*Number of canes/pot*.—3.

*Cane color*.—Sun exposed canes RHS N79A; shaded canes RHS 144A.

*Spines* (*present or absent*).—Absent.

*Bud shape*.—Elliptic. Length: 0.85 cm. Diameter (base): 0.40 cm. Diameter (tip): 0.10 cm. Color: undertone RHS 145A, overtone RHS 70A. Texture: Mildly pubescent.

Floricanes:

*Cane shape in cross-section*.—Rounded to Angular.

*Diameter*.—Base: 1.3 cm|Middle: 1.1 cm|Tip: 1.0 cm.

*Length*.—99.1 cm.

*Number of nodes*.—15.

*Internode length*.—Base: 5.8 cm|Middle: 5.7 cm|Tip: 5.2 cm.

*Cane color*.—Lower Cane — RHS 146B. Upper Cane — RHS 146B.

*Spines*.—Absent.

*Bud shape*.—Elliptic. Length: 0.51 cm. Diameter (base): 0.14 cm. Diameter (tip): 0.09 cm. Color: RHS 145A, overtone RHS 70A. Texture: Mildly pubescent.

*Winter hardiness*.—Unknown for 'HFG B1902T' outside of USDA Hardiness Zone 9b (Watsonville, Santa Cruz County, California, USA). This cultivar is best adapted to the mild coastal conditions of California.

*Drought/heat tolerance*.—Pollen viability and fruit quality of blackberry generally begins to decline above 30° C. 'HFG B1902T' has not been tested under temperatures above 30° C. Blackberries are generally drought tolerant, however 'HFG B1902T' has not been tested under unirrigated conditions.

Leaves:

*Primocane leaves*.—

*Complete leaf*.—Leaf Shape in Cross-section: Simple cordate leaflet. Length: 21.3 cm. Width: 26.1 cm. Number of leaflets: 5. Shape of leaf: Palmate. Apex: Convex. Shape of leaf base:. Terminal leaf: Mildly Cordate. Distal lateral leaflets: Mildly Cordate. Basal lateral leaflets: Mildly Cordate. Margin: Triply Serrate. Texture: Moderate interveinal blistering. Number of serrations/leaf: 144.

*Shape of serrations*.—Concave — Flexuous. Color: Primocane Upper Surface: RHS N137B. Primocane Lower Surface: RHS 147B. Venation pattern: Palmate. Venation Color: Upper surface: RHS 137B. Lower surface: RHS 146D. Leaf pubescence density: Moderate. Color of leaf pubescence: Primocane — RHS 146B. Interveinal blistering: Present, moderate. Glossiness: Present, Low. Petiole length: 6.3 cm. Petiole diameter: 0.37 cm. Petiole Color: Upper: Undertone RHS 145A; Overtone RHS 183A. Lower: Undertone RHS 145A; Overtone RHS 184B. Rachis length: 2.3 cm. Rachis Diameter: 0.25 cm. Stipule length: 1.1 cm. Stipules per leaf: 2. Stipule Width: 0.08 cm.

*Stipule color*.—RHS 144A. Upper Surface: RHS N137B. Lower Surface: RHS 147B.

*Terminal leaflet*.—Length: 12.4 cm. Width: 10.7 cm. Length/Width ratio: 1.16Rachis length: 2.3 cm.

*Distal lateral leaflet*.—Length: 12.4 cm. Width: 9.4 cm. Length/Width ratio: 1.32. Petiolule length: 1.21 cm.

*Basal lateral leaflet*.—Length: 9.0 cm. Width: 6.0 cm. Length/Width ratio: 1.50. Petiolule length: 0.35 cm.

*Floricane leaves*.—

*Complete leaf*.—Leaf Shape in Cross-section: Simple cordate leaflet. Length: 16.4 cm. Width: 16.9 cm. Number of leaflets: 3. Shape of leaf: Palmate. Apex: Convex. Shape of leaf base: Terminal leaf: Mildly Cordate. Basal lateral leaflets: Mildly Cordate. Margin: Doubly Serrate. Texture: Moderate interveinal blistering. Number of serrations/leaf: 89. Shape of serrations: Concave-Flexuous. Terminal leaflet color: Upper surface: RHS N137A. Lower surface: RHS 147B. Length: 8.4 cm. Width: 6.1 cm. Color: Upper surface: RHS N137A. Lower surface: RHS 147B. Venation pattern: Palmate. Venation Color: Upper surface: RHS N137A. Lower surface: RHS 145B. Leaf pubescence density: Moderate. Color of leaf pubescence: RHS 145C. Interveinal blistering: Present, moderate. Glossiness: Present, Low. Petiole length: 4.0 cm. Stipule length: 0.8 cm. Stipules per leaf: 2. Stipule Width: 0.1 cm. Stipule Color: RHS 146A. Color: Upper surface: RHS N137A. Lower surface: RHS 147B.

*Terminal leaflet*.—Length: 9.9 cm. Width: 7.5 cm. Length/Width ratio: 1.32. Rachis Length: 2.3 cm.

*Distal lateral leaflet*.—Length: N/A. Width: N/A.

*Basal lateral leaflet*.—Length: 8.4 cm. Width: 6.1 cm. Length/Width ratio: 1.38.

*Petiolule*.—Length: 0.3 cm. Diameter: 0.17 cm. Color: Upper surface: RHS 146D. Lower surface: RHS 146D.

Flowers:

*Time of flowering* (50% *of plants at first flower*).—April 5.

*Size*.—Length: 0.9 cm. Diameter: 4.4 cm.

*Fragrance*.—Lightly floral rose scent.

*Peduncle*.—Length: 8.5 cm. Diameter: 0.15 cm. Color: Upper — RHS 148A. Lower — RHS 146C. Pubescence: Puberulent. Texture: Soft.

*Perianth*.—Flowering trusses shape: Truncate.

*Petals*.—Color Upper: RHS N155A. Lower: RHS N155C. Number per flower: 5. Shape: Obovate. Length: 2.1 cm. Width: 1.2 cm. Apex descriptor: Complex. Base Descriptor: Decurrent. Margin descriptor: Entire. Texture: Smooth with visible striations.

*Sepals*.—Quantity: 5. Length: 0.69 cm. Width: Base: 0.55 cm|Mid: 0.49 cm|Tip: 0.17 cm. Color: Upper is RHS 146B; lower is RHS 148C. Apex descriptor: Acuminate. Margin descriptor: Entire. Texture: Puberulent.

*Pedicel*.—Color: undertone — RHS 146B, overtone — RHS N77A. Length: 3.1 cm. Diameter: 0.09 cm.

Reproductive organs:

*Self-fertile*.—Yes.

*Male*.—Stamen number: 122. Filament Length: 0.8 cm. Diameter: 0.1 cm. Color: RHS 157B.

*Anther length*.—0.1 cm. Diameter: 0.1 cm. Color: RHS 145C.

*Pollen color*.—RHS 152C. Amount: Heavy.

*Female*.—

*Style*.—Length: 0.35 cm. Diameter: 0.01 cm. Color: RHS 144C.

*Stigma*.—Length: 0.01 cm. Diameter: 0.01 cm. Color: RHS 145B.

*Ovary*.—Length: 0.2 mm. Diameter: 0.03 mm. Color: RHS 145C.

Fruit:

*Predominant shape*.—Medium Ovate.

*Weight*.—7.5 g.

*Length*.—3.5 cm.

*Width*.—2.0 cm.

*Length/width ratio*.—1.75.

*Receptacle*.—Length.—2.8 cm. Diameter: Base: 0.9 cm|Middle: 0.7 cm|Tip: 0.5 cm. Color: RHS 60A.

*Drupelet*.—Length: 0.7 cm. Diameter: 0.5 cm. Number: 84. Drupelet weight: 0.09 g.

*Fruit color*.—External: RHS 203A. Internal: RHS 203A. Firmness of fruit skin: Very firm. Firmness of fruit flesh: Very firm. Hollow center: Absent (torus present in blackberries). Number of fruit per node: 20 on a fruiting lateral. Time of ripening (50% of plants with first fruit): 15 May on floricanes. Time of fruiting: Early-Mid. Type of bearing: Floricane.

*Fruit yield*.—Floricanes: 20,000 lb/a. Primocanes: N/A. Average brix: 12.9. Market use: Fresh. Keeping quality: Excellent. Shipping quality: Excellent.

Pest and disease resistance: Field and substrate trials of 'HFG B1902T' have shown tolerance to *Agrobacterium tumefaciens*, and *Botrytis*. 'HFG B1902T' is susceptible to downy mildew (*Peronospora sparsa*) and powdery mildew (*Sphaerotheca macularis*), under cool, wet springtime conditions.

What is claimed is:

1. A new and distinct cultivar of Blackberry plant named 'HFG B1902T' as described and shown herein.

* * * * *